US007235794B2

(12) United States Patent
Sender et al.

(10) Patent No.: US 7,235,794 B2
(45) Date of Patent: Jun. 26, 2007

(54) SYSTEM AND METHOD FOR INSPECTING CHARGED PARTICLE RESPONSIVE RESIST

(75) Inventors: Benzion Sender, Modiin (IL); Ophir Dror, Shoham (IL); Guy Eytan, Menora (IL)

(73) Assignee: Applied Materials, Inc., Santa Claa, CA (US)

( * ) Notice: Subject to any disclaimer, the term of this patent is extended or adjusted under 35 U.S.C. 154(b) by 0 days.

(21) Appl. No.: 10/893,614

(22) Filed: Jul. 16, 2004

(65) Prior Publication Data

US 2005/0067582 A1    Mar. 31, 2005

Related U.S. Application Data

(63) Continuation of application No. 10/683,192, filed on Oct. 10, 2003, now abandoned, which is a continuation of application No. 10/352,590, filed on Jan. 27, 2003, now abandoned.

(60) Provisional application No. 60/354,260, filed on Feb. 4, 2002.

(51) Int. Cl.
*A61N 5/00* (2006.01)
*G21G 5/00* (2006.01)
*G21K 5/10* (2006.01)
*H01J 37/08* (2006.01)
*G01N 23/00* (2006.01)

(52) U.S. Cl. ............................. 250/492.2; 250/492.2; 250/492.22; 250/307; 250/310; 430/296

(58) Field of Classification Search ............... 250/310, 250/311, 492.1, 492.22, 492.2, 307; 430/296
See application file for complete search history.

(56) References Cited

U.S. PATENT DOCUMENTS 5,302,828 A    4/1994    Monahan (Continued)

FOREIGN PATENT DOCUMENTS

WO    01/78103 A    10/2001

OTHER PUBLICATIONS

Wu et al., "Investigation on the Mechanism of the 193 nm Resist Linewidth Reduction During the SEM Measurement", Proceedings of SPIE, vol. 4345, Feb. 2001, pp. 190-199.

(Continued)

*Primary Examiner*—David A. Vanore
(74) *Attorney, Agent, or Firm*—Tarek N. Fahmi

(57) ABSTRACT

An apparatus and method for scanning a pattern. The method includes: (i) directing a charged particle beam such as to interact with the pattern along a first scan path, and (ii) directing a beam such as to interact with the pattern along a second scan path. The pattern changes one of its characteristics as a result of an interaction with the beam. The distance between the first and the second scan paths may be bigger than the diameter of the charged electron beam. Each of the first and second scan paths may include a plurality of consecutive samples and the distance between the first and second scan paths may be bigger than a distance between adjacent samples. The location of scan paths may be changed between measurements and especially between measurement sessions. The charged particle beam may have an ellipsoid cross section.

24 Claims, 10 Drawing Sheets

U.S. PATENT DOCUMENTS 5,304,811 A * 4/1994 Yamada et al. ........ 250/492.22
5,576,833 A 11/1996 Miyoshi et al.
6,037,601 A * 3/2000 Okunuki ................ 250/492.23
6,727,507 B2 * 4/2004 Shimazu et al. ......... 250/492.1
6,737,658 B1 * 5/2004 Nakasugi et al. ...... 250/492.22
6,855,929 B2 * 2/2005 Kimba et al. ............... 250/310
2003/0132197 A1 * 7/2003 Ke et al. ...................... 216/67

OTHER PUBLICATIONS

International Search Report for PCT/US03/02415, mailed Jul. 18, 2003, 7 pages.

* cited by examiner

```
┌─────────────────────────────────────────┐
│   LOCATING A PATTERN TO BE INSPECTED    │
│                  182                    │
└─────────────────────────────────────────┘
                    │
┌─────────────────────────────────────────────────────┐
│ DIRECTING A CHARGED PARTICLE BEAM SUCH AS TO INTERACT│
│ WITH THE PATTERN ALONG A SCAN PATH. THE BEAM IS SHAPED│
│ ACCORDING TO A RECTANGULAR PIXEL. THE PATTERN CHANGES│
│   ONE OF ITS CHARACTERISTICS AS A RESULT OF AN      │
│       INTERACTION WITH THE CHARGED PARTICLE BEAM    │
│                         184                         │
└─────────────────────────────────────────────────────┘
                    │
┌─────────────────────────────────────────────────────┐
│  COLLECTING ELECTRONS SCATTERED AS A RESULT OF THE  │
│  INTERACTION BETWEEN THE CHARGED PARTICLE BEAM AND  │
│   THE RESIST AND PROCESSING THE DETECTED ELECTRONS  │
│            TO PROVIDE A WIDTH MEASUREMENT           │
│                         186                         │
└─────────────────────────────────────────────────────┘
                    │
┌─────────────────────────────────────────────────────┐
│ DIRECTING A CHARGED PARTICLE BEAM SUCH AS TO INTERACT│
│  WITH THE PATTERN ALONG A SCAN PATH SUCH AS A SECOND│
│                      SCAN PATH.                     │
│                         188                         │
└─────────────────────────────────────────────────────┘
                    │
┌─────────────────────────────────────────────────────┐
│  COLLECTING ELECTRONS SCATTERED AS A RESULT OF THE  │
│  INTERACTION BETWEEN THE CHARGED PARTICLE BEAM AND  │
│   THE RESIST AND PROCESSING THE DETECTED ELECTRONS  │
│          TO PROVIDE ANOTHER WIDTH MEASUREMENT       │
│                         190                         │
└─────────────────────────────────────────────────────┘

SYSTEM AND METHOD FOR INSPECTING CHARGED PARTICLE RESPONSIVE RESIST

RELATED APPLICATIONS

This is a continuation of U.S. patent appliction Ser. No. 10/683,192, entitled "System and Method for Inspecting Charged Particle Responsive Resist", filed on Oct. 10, 2003 now abandoned, which is a continuation of U.S. patent application Ser. No. 10/352,590, filed on Jan. 27, 2003 now abandoned, which claims the priority benefit of U.S. provisional application 60/354,260, filed 4 Feb. 2002, entitled "A system and method for reducing resist layer shrinkage resulting from charged particle beam". This patent application is hereby incorporated by reference in its entirety.

FIELD OF THE INVENTION

This invention relates to an apparatus and method for inspecting semiconductors wafers during circuit fabrication and, in particular, for inspecting resistive materials that respond to charged particle beams.

BACKGROUND OF THE INVENTION

Integrated circuits are very complex devices that include multiple layers. Each layer may include conductive material and/or isolating material while other layers may include semi-conductive materials. These various materials are arranged in patterns, usually in accordance with the expected functionality of the integrated circuit. The patterns also reflect the manufacturing process of the integrated circuits.

Integrated circuits are manufactured by complex multi-staged manufacturing processes. During these multi-staged processes, resistive material is (i) deposited on a substrate/layer, (ii) exposed by a photolithographic process, and (iii) developed to produce a pattern which defines some areas to be later etched.

Resistive materials are usually selected such as to be responsive to a light at a predefined narrow range of frequencies (wavelengths). A commonly utilized resistive material is responsive to 193 nm light emitted from ArF light sources. This resistive material is referred to as 193 nm resist.

Various inspection and failure analysis techniques evolved for inspecting integrated circuits both during the fabrication stages and between consecutive manufacturing stages, either in combination with the manufacturing process (also termed "in line" inspection techniques) or not (also termed "off line" inspection techniques). Various optical as well as charged particle beam inspection tools and review tools are known in the art, such as the VeraSEM™, Compluss™ and SEMVision™ tools of Applied Materials Inc. of Santa Clara, Calif.

Manufacturing failures may affect the electrical characteristics of the integrated circuits. Some of these failures result from unwanted deviations from the required dimensions of the patterns. A "critical dimension" is the width of a patterned line or the distance between two patterned lines.

One of the goals of the inspection process is to determine whether the inspected wafer includes deviations from these critical dimensions. This inspection is usually done by charged particles beam imaging that provides the high resolution required to measure said deviations.

Various resistive materials are also responsive to charged particle beams, such as electrical beams emitted during scanning electron microscope (SEM) imaging. For example, the 193 nm resist shrinks as result of an interaction with the electron beam. The shrinkage is due to both quantum effects (breaking of chemical bonds) and localized heating effects. Thus, SEM imaging causes an unwanted change in the pattern imprinted upon a semiconductor.

SUMMARY OF THE INVENTION

The present invention provides various scanning schemes that enable to charged particle imaging while reducing the unwanted side effects of said imaging and measurements.

According to an aspect of the invention resist shrinkage is reduced by a reduction of an imaging charge density resulting from an interaction between an electron beam and the resistive material.

According to one embodiment of the invention, a first scanning scheme involves scanning with an electron beam along multiple parallel scan paths, wherein the distance between two adjacent scan paths is much larger than the diameter of the electron beam.

According to another embodiment of the invention, the scanning paths are included within scanning windows. The scanning windows are spaced apart from each other and may be defined in response to the spectral analysis of line width variations. According to a further aspect of the invention, the spacing between adjacent scan paths within a scanning window is responsive to a high spatial frequency component of said line width variation. In other words, the sampling along the line should satisfy the line variation along the line (line roughness) to facilitate a determination of line variations without losing roughness information that may generate loss of precision due to aliasing effects.

According to yet a further aspect of the invention, the width of a scanning window is responsive to a low spatial frequency component of the line width variation.

In many scanning devices the scanning paths define pixels—each scan path includes multiple samples—each sample is defined as a pixel. Such a pixel has a length that substantially equals the distance between two adjacent scan paths, and has a width that corresponds to a distance that the electron beam passes between two consecutive samples. Accordingly, if the distance between two adjacent scan paths is bigger than the distance that the electron beam passes between two consecutive samples, the pixel is rectangular.

Thus, scanning the resistive material with rectangular pixels reduces the electron beam flux in a direction perpendicular to scan direction, and accordingly reduces the shrinkage. The rectangular pixels may be further arranged to provide an image.

The invention thus provides a method for scanning a pattern with a charged particle beam, the method includes: (i) directing a charged particle beam such as to interact with the pattern along a first scan path, wherein the pattern changes one of its characteristics as a result of an interaction with the charged particle beam; and (ii) directing a charged particle beam such as to interact with the pattern along a second scan path, wherein the distance between the first scan path and the second scan path is bigger than the diameter of the charged electron beam.

The invention also provides a further method for scanning a pattern with a charged particle beam, this method including: (i) directing a charged particle beam such as to interact with the pattern along a first scan path, wherein the pattern changes one of its characteristics as a result of an interaction with the charged particle beam; and (ii) directing the charged particle beam such as to interact with the pattern along a second scan path, wherein each of the first and second scan paths comprise a plurality of consecutive samples, and wherein the distance between the first scan path and the second scan path is bigger than a distance between adjacent samples.

According to still another embodiment of the invention, the distance between adjacent scan paths is changed during the SEM imaging process. Accordingly, if the pattern is re-imaged, the electron beams do not follow the same track as previous electron beams. Different beam positioning within the rectangular pixel allows for reduced shrinkage in cases of measurement re-visit.

The invention also provides a method for scanning a pattern with a charged particle beam, which method includes: (i) directing a charged particle beam such as to interact with the pattern along a first scan path, wherein the pattern changes one of its characteristics as a result of an interaction with the charged particle beam; (ii) directing the charged particle beam such as to interact with the pattern along a second scan path; and (iii) changing the distance between the first scan pattern path and the second scan path and repeating the steps of directing a charged particle beam.

According to still a further embodiment of the invention, the electronic beam is defocused (preferably within the limits of a predefined pixel). The defocusing results in a relatively large spot that interacts with the resistive layer.

The invention thus provides a method for scanning a pattern with a charged particle beam, which method includes: (i) directing a charged particle beam such as to interact with the pattern along a first scan path, wherein the pattern changes one of its characteristics as a result of an interaction with the charged particle beam, the charged particle beam having a ellipsoid cross section; and (ii) directing the charged particle beam such as to interact with the pattern along a second scan path.

Moreover, the invention provides an apparatus for scanning a pattern with a charged particle beam, the apparatus including means for generating a charged particle beam; and means for directing a charged particle beam such as to interact with the pattern along a first scan path. The pattern changes one of its characteristics as a result of an interaction with the charged particle beam. The means for directing are further operable to direct the charged particle beam such as to interact with the pattern along a second scan path, wherein the distance between the first scan path and the second scan path is bigger than the diameter of the charged electron beam.

The invention also provides an apparatus for scanning a pattern with a charged particle beam, which apparatus includes means for generating the charged particle beam; and means for directing the charged particle beam such as to interact with the pattern along a first scan path. The pattern changes one of its characteristics as a result of an interaction with the charged particle beam. The means for directing are further operable to direct the charged particle beam such as to interact with the pattern along a second scan path. Each of the first and second scan paths comprise a plurality of consecutive samples and the distance between the first scan path and the second scan path is bigger than a distance between adjacent samples.

The invention further provides an apparatus for scanning a pattern with a charged particle beam, which apparatus includes means for generating a charged particle beam; and means for directing a charged particle beam such as to interact with the pattern along a first scan path. The pattern changes one of its characteristics as a result of an interaction with the charged particle beam. The means for directing are further operable to direct the charged particle beam such as to interact with the pattern along a second scan path and are also operable to change the location of the first scan path and the second scan path and to repeat the steps of directing a charged particle beam.

The invention additionally provides an apparatus for scanning a pattern with a charged particle beam. The apparatus includes means for generating an ellipsoid cross-sectioned charged particle beam; and means for directing the charged particle beam such as to interact with the pattern along a first scan path. The pattern changes one of its characteristics as a result of an interaction with the charged particle beam. The means for directing are further operable to direct the charged particle beam such as to interact with the pattern along a second scan path.

At least some of the embodiments may be combined. For example, scanning may be performed in different beam positions within a rectangular pixel for re-visits and/or de-focusing of the beam may resuls in a spot that will cover the width of two rectangular pixels.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 7–10 are flow charts illustrating methods for imaging charged particle responsive resists in accordance with embodiments of the invention.

DETAILED DESCRIPTION OF THE DRAWINGS

The following description relates to charged particle microscopes, such as SEMs, including step and repeat type SEMs in which a wafer is scanned by repetitive steps of scanning an area of the wafer (said area defined by the field of view of the SEM) and mechanically introducing a movement between the wafer and SEM to facilitate the scanning of another area. Said movement may also be implemented by electrostatic and/or magnetic fields introduced by various electrostatic and/or magnetic elements such as lenses, deflectors and the like. It is noted that other charged particles and even photons may be utilized for detecting voltage contrast. It is further noted that this invention may also be implemented by introducing a substantially constant movement between the SEM and the wafer. The movement may be linear or even rotational, and/or any combination of both movements.

Figure 1:
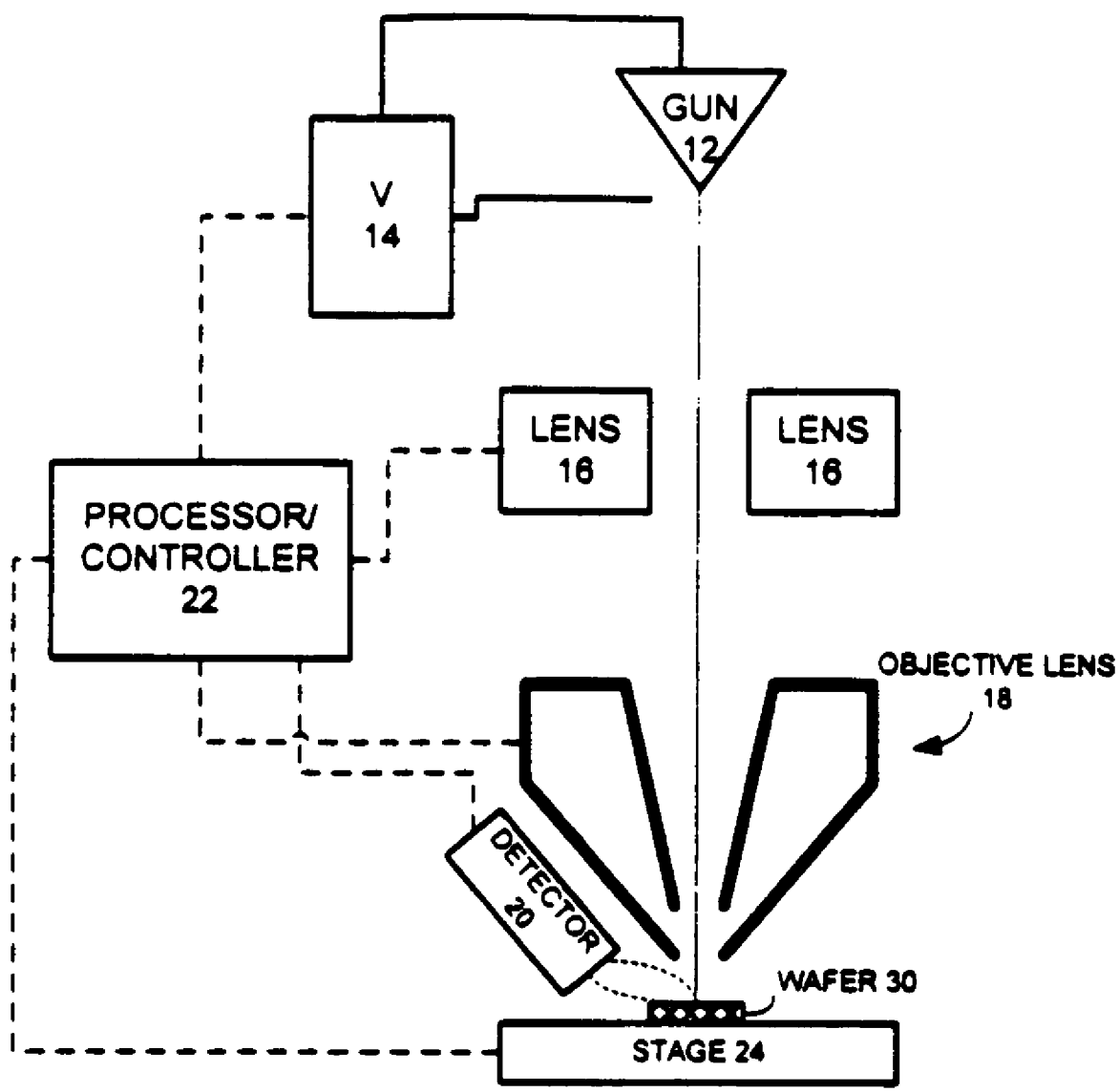
FIG. 1 is a schematic illustration of a scanning electron microscope, in accordance with an embodiment of the invention.

Referring to FIG. 1 a SEM 10 configured in accordance with an embodiment of the invention is illustrated. SEM 10 includes electron gun 12, subjected to various voltages, such as an acceleration voltage that is schematically described as acceleration power source 14, first electron lens 16, magnetic-electrostatic objective lens 18, detector 20, controller/processor 22 and stage 24. Lenses 16 and 18 are controlled by controller/processor 22 to focus, direct and scan the charged particle beam. They may also be operable to shape the charged particle beam in manners known in the art. Each of said components/units is well known in the art thus do not require a detailed description. Briefly, SEM 10 is operable to generate a charged particle beam (especially by means of electron gun 12 and power source 14), to direct and focus the beam onto a specimen (such as wafer 30, which may be placed onto stage 24) and to scan the charged particle beam.

Figure 2:
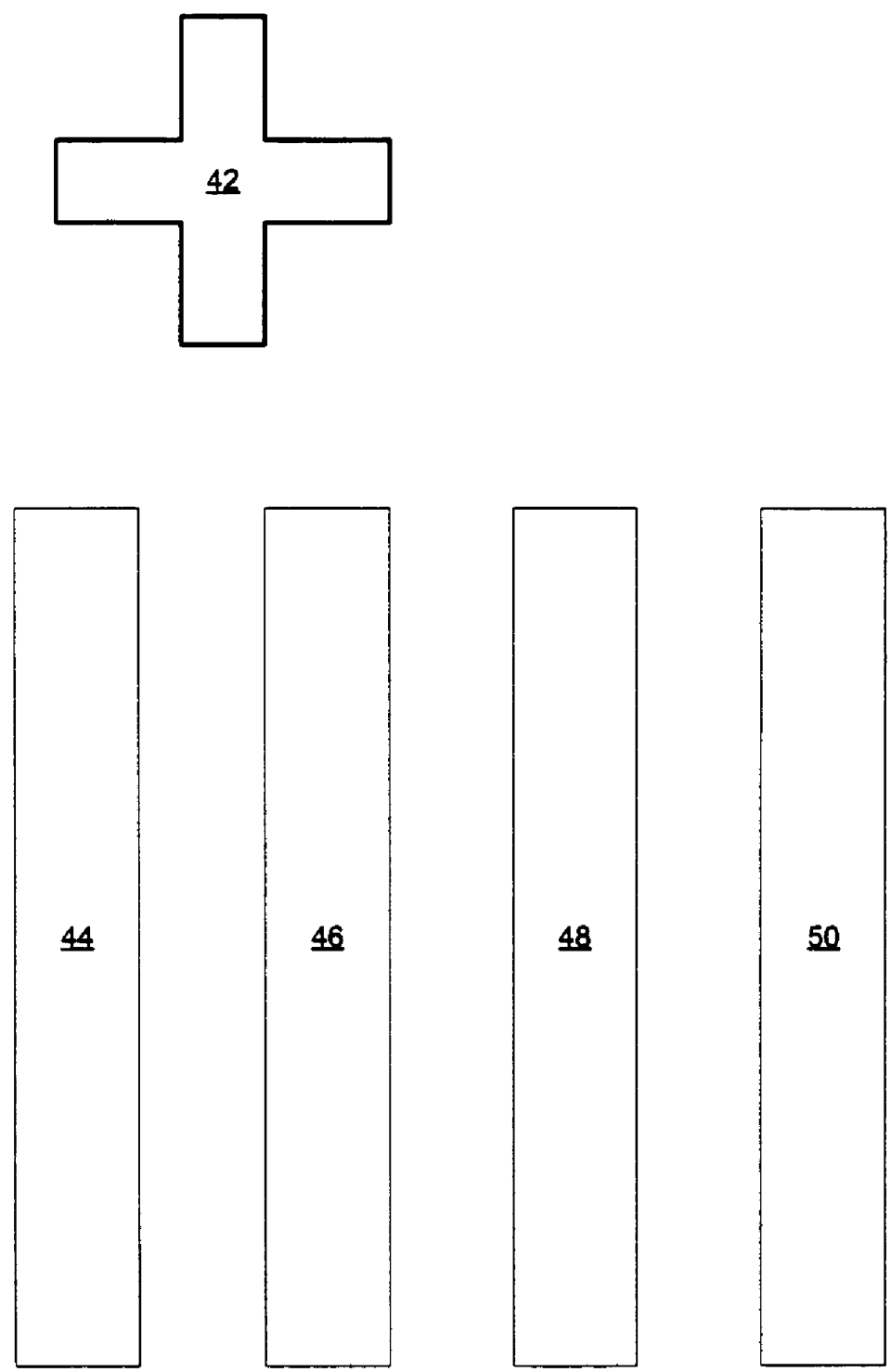
FIG. 2 is a schematic illustration of a portion of an inspected wafer, in accordance with an embodiment of the invention.

Referring to FIG. 2 a portion 40 of wafer 30 is illustrated. Portion 40 includes an alignment cross-shaped target 42, and multiple vertical lines 44–50. The width of a certain line 44, as well as the distances between lines may be measured by one of the schemes mentioned below. Usually, before the width of a certain line is measured that certain line has to be located. Said location may be roughly known in advance, whereas target 42 assists in locating the certain line. Conveniently, determining the location includes generating a low-resolution image of portion 40. For example, portion 40 may be imaged by 480×480 pixels of 0.5×0.5 micron$^2$ pixels, while critical dimension measurement pixel dimensions width is about few nanometers.

Figure 3:
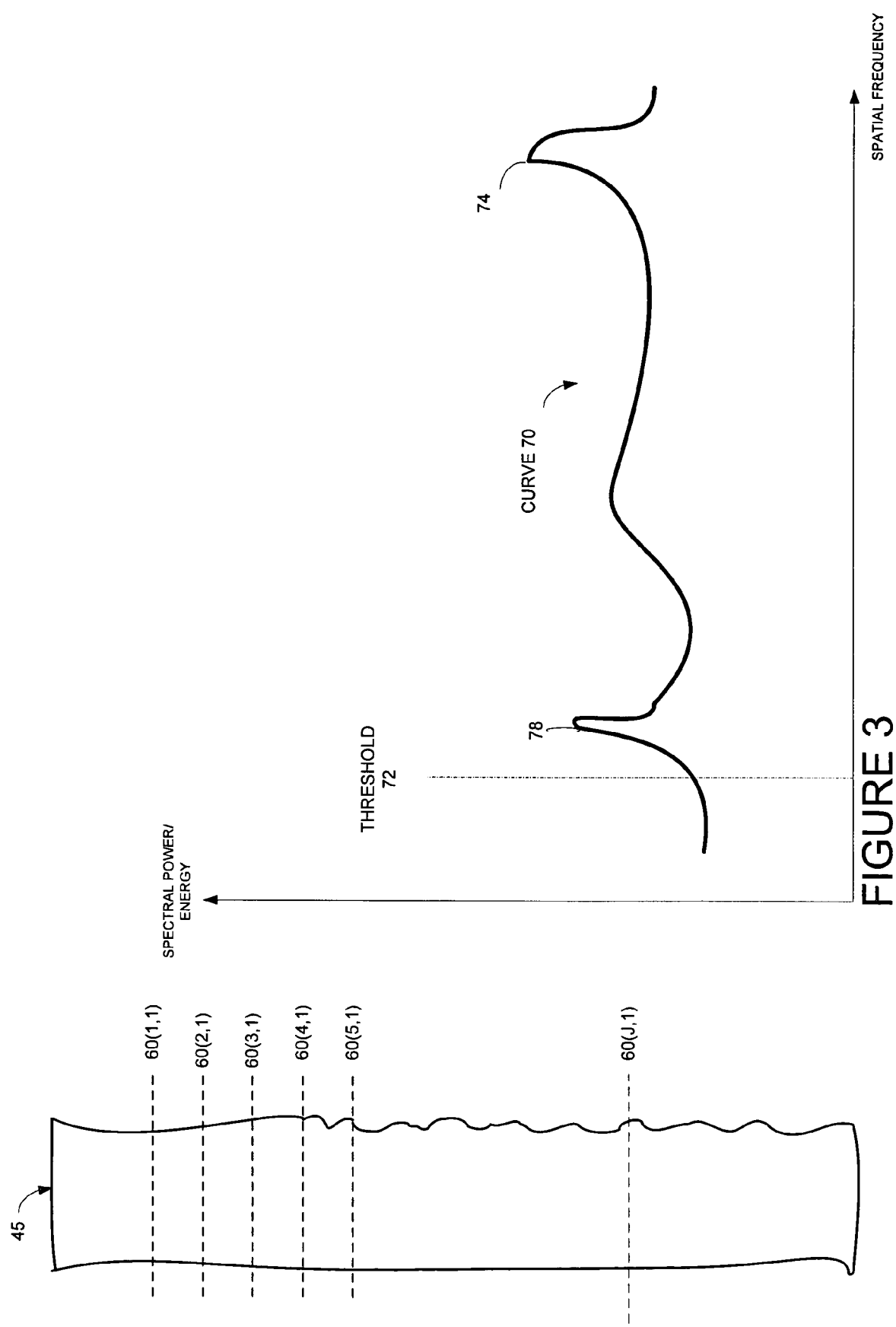
FIG. 3 is a schematic illustration of a spectral representation of line widths of a certain line of the portion of FIG. 2, in accordance with an embodiment of the invention.

Referring to FIG. 3, a section 45 of line 44 and a spectral representation of line width variations (also termed line width roughness) are illustrated in greater details in accordance with an aspect of the invention. Said spectral representation may be generated by converting multiple line width measurements (from distinct vertical locations) of line 44 by Fast Fourier Transform, although other means (such as cross correlation techniques) for implementing said conversion may be applied.

The width of line 44 is measured by multiple measurements 60(j,k), where k is a positive integer identifying the measurement session and j ranges between 1 and J, J having a predefined value that may be defined in accordance with various accuracy, signal to noise ratio and/or consistency requirements. The number of scan lines may be defined by a user, and may range between few lines to even a thousand lines. The number of lines is defined by the ratio between a length of a scanning window and the vertical displacement between two adjacent scan lines. It is further noted that the number of pixels per scan path may also vary. A typical scan line includes between 240 and 960 pixels.

Curve 70 illustrates the spectral representation of the line width roughness and includes many spatial frequency components, such as low spatial frequency (Dlow) component 78 and high spatial frequency (D high) component 74, whereas each component includes a substantial amount of spectral energy. High spatial frequency component 74 will define the distance between adjacent scan paths while the low spatial frequency component 78 will define the width of a scanning window, such to enable repetitive critical dimension measurements.

In many cases a high spatial frequency threshold (such as threshold 72) is provided. This may represent the manufacturing process limitations and more specifically a limited ability to compensate for very high spatial frequency line width variations. Accordingly, frequencies above the threshold are disregarded. Typically, the high spatial frequency threshold is set at about fifty nanometers, but future manufacturing techniques are expected to reduce that threshold.

First Embodiment

Figure 4:
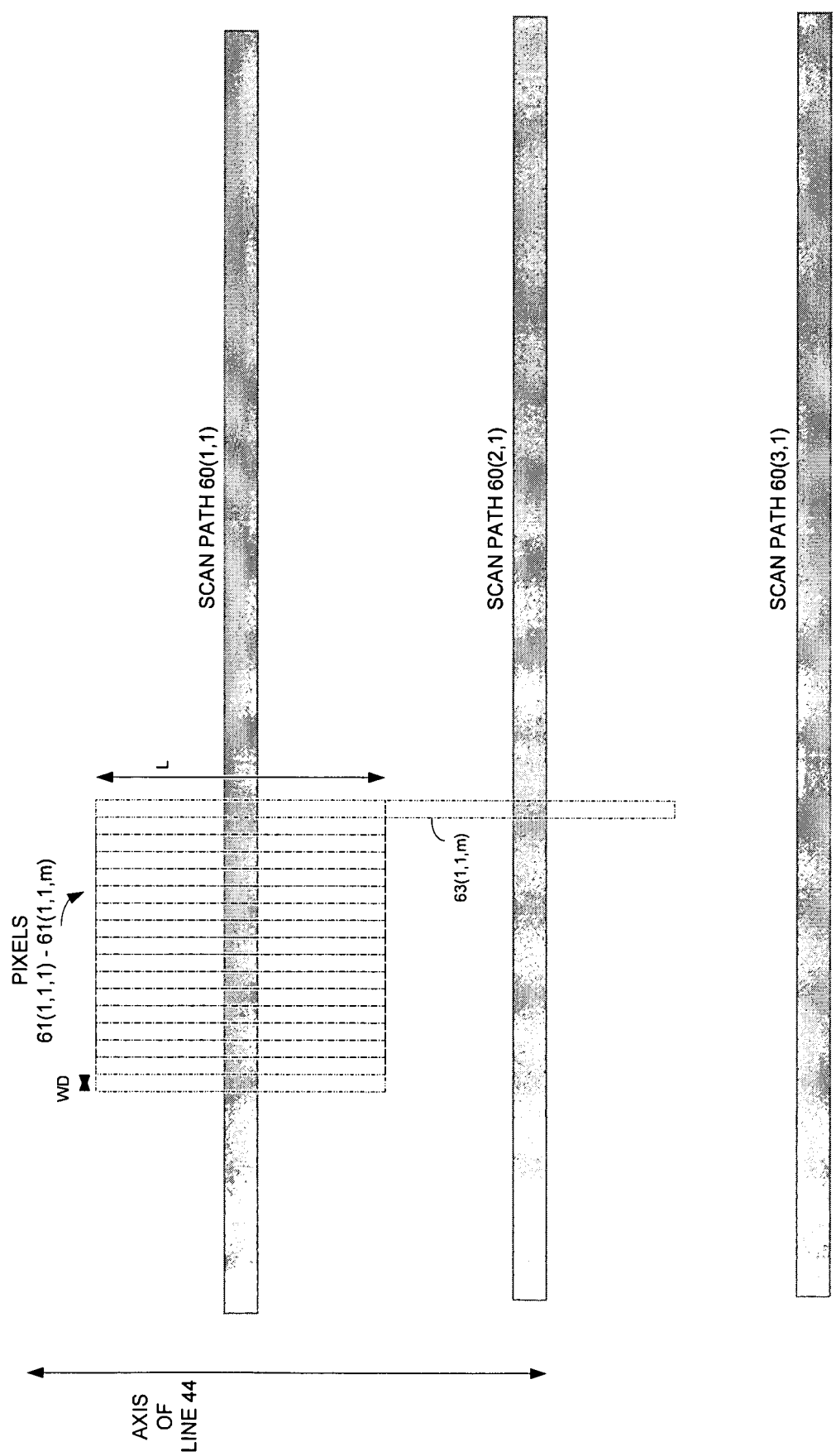
FIGS. 4–6 illustrate various scanning schemes, in accordance with embodiments of the invention.

Referring to FIG. 4, a first embodiment of the invention is illustrated. A section of line 44 is scanned by horizontal scan paths, such as scan paths 60(1,1)–60(3,1). The horizontal displacement between consecutive pixels 61(1,1,1)–61(1,1,m) of scan path 60(1,1) are much smaller than the vertical displacement between scan path 60(1,1) and an adjacent scan path 60(2,1). In other words, each pixel, such as pixel 61(1,1,1,) are rectangular, the width WD of pixel 61(1,1,1) can be approximately less than a nanometer or a few nanometers long, while its length L (height) may exceed even hundreds of nanometers. It is noted that further pixels are illustrated.

Usually, the pixel's width WD is defined in response to a required SEM resolution. It may be substantially equal to the beam spot diameter. The pixel length may be responsive to various factors such as a predefined shrinkage reduction level (inversely proportional to L), line width roughness spectrum, and especially to the low frequency component, and to other factors. Typically, the pixel width WD is about few nanometers, while the height may be about twenty-five nanometers up to a few microns.

In order to track line width variations, the distance between two consecutive scan paths (the pixel width) should be responsive to the line variation along the line (line roughness), and especially to the high spatial frequency component 74. If we denote the spatial frequency of the high spatial frequency component 74 by $D_{high}$ then the length of each pixel shall be equal to or smaller than $D_{high}/2$. The width of the pixel is defied in response to the system required resolution.

According to an aspect of the invention the scan paths are included within scanning windows. The height of a scanning window may be responsive to the spatial frequency $D_{low}$ of the low spatial frequency component 78. The repeatability of critical dimension measurements is increased by selecting a width that is greater than or substantially equal to the spatial frequency of low spatial frequency component 78.

Figure 7:
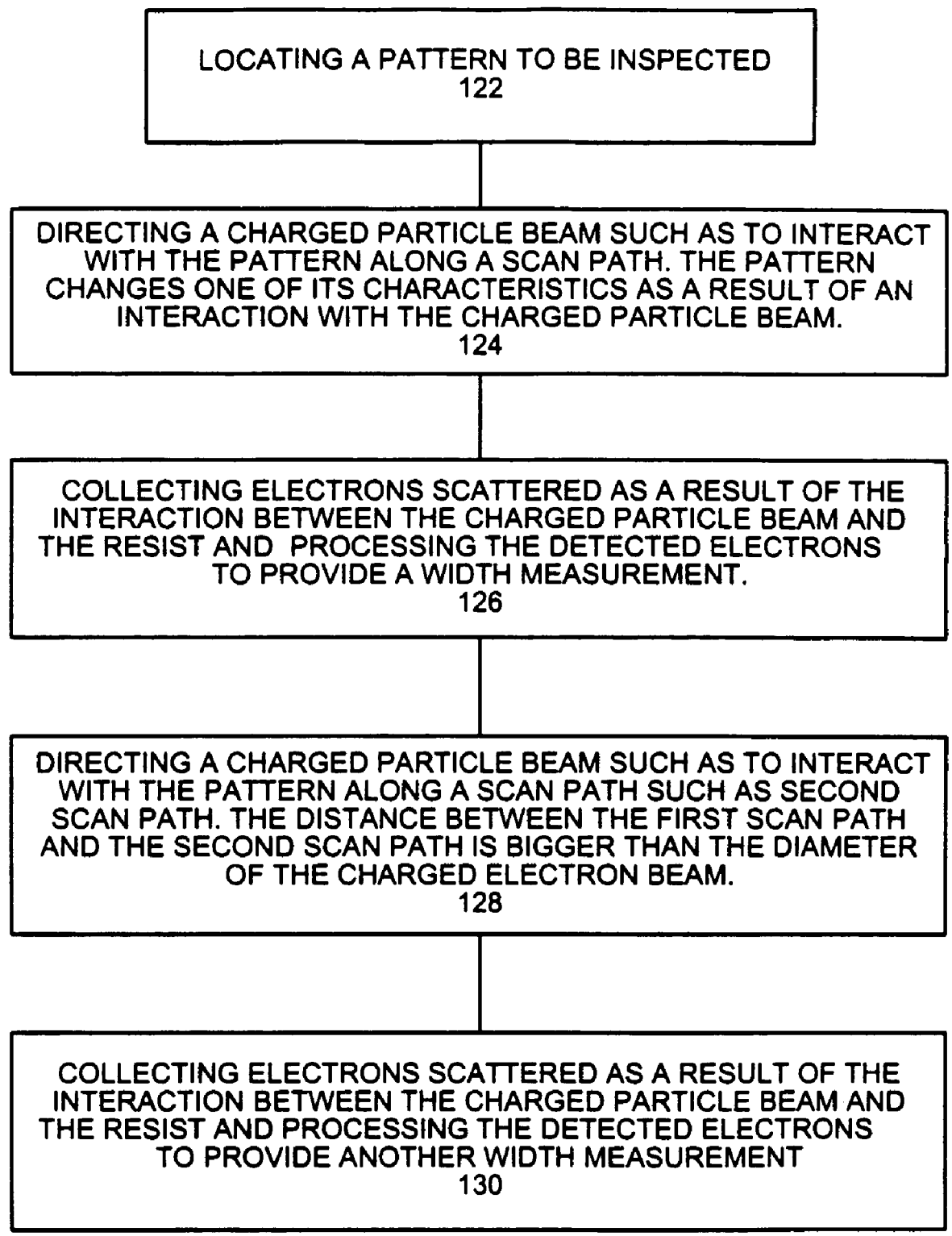
Figure 8:
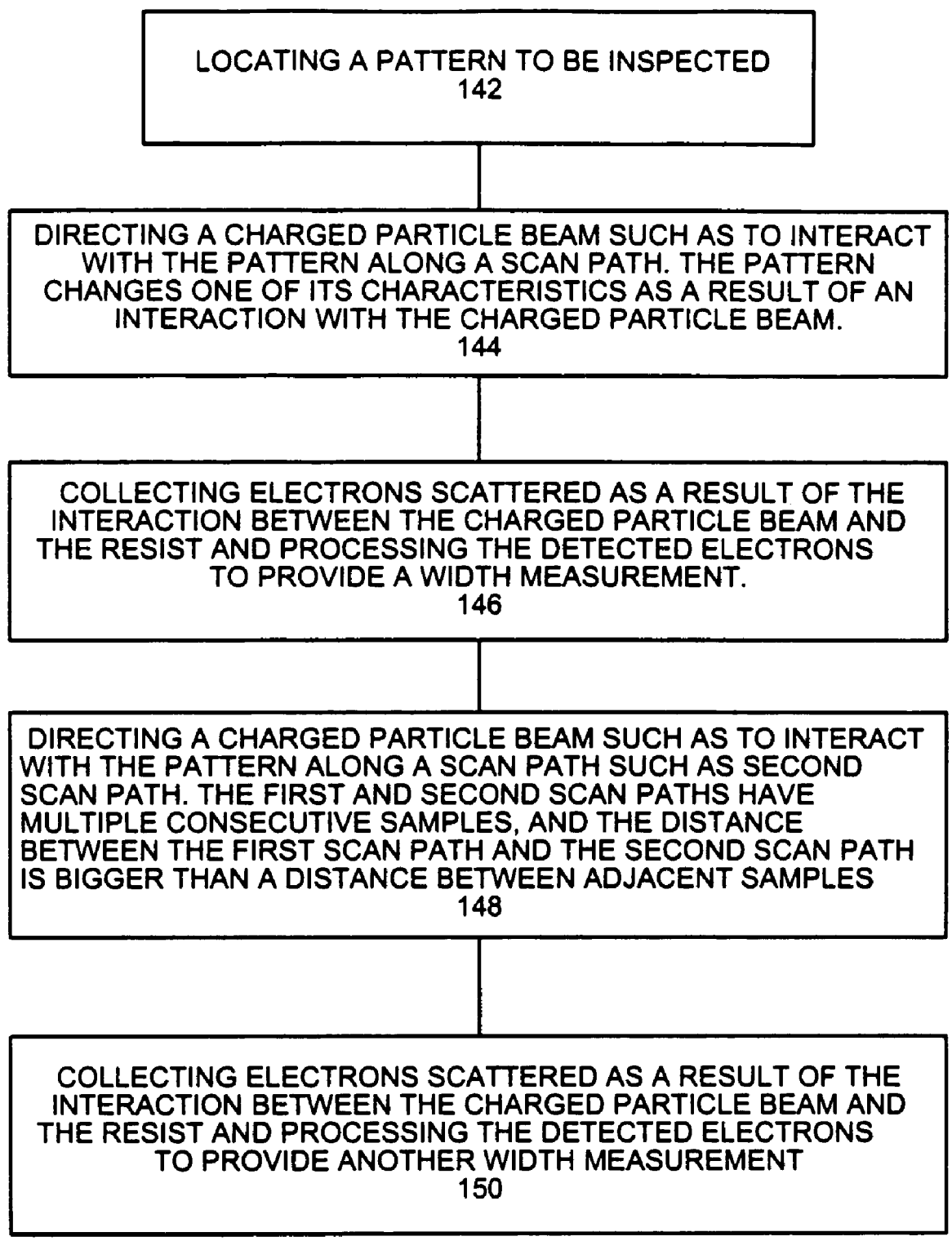

Referring to FIGS. 7–8, methods 120 and 140 in accordance with aspects of the invention are illustrated. Method 120 starts by step 122 of locating a pattern to be inspected, conveniently to have one of its dimensions measured. Referring to previous examples, section 45 of line 44 is to be inspected in order to measure the width of line 44.

Step 122 is followed by step 124 of directing a charged particle beam such as to interact with the pattern along a scan path such as first scan path 60(1,1). The pattern changes one of its characteristics as a result of an interaction with the charged particle beam. Referring to previous exemplary figures, SEM 10 directs a charged electron beam towards wafer 30 to interact with a section 45 of line 44 along scan path 60(1,1). It is noted that scan path 60(1,1) further interacts with other lines of portion 40. The change of characteristics is a shrinkage of the resist that forms line 44.

Step 124 is followed by step 126 of collecting electrons scattered as a result of the interaction between the charged particle beam and the resist and of processing the detected electrons to provide a width measurement.

Step 126 is followed by step 128 of directing a charged particle beam such as to interact with the pattern along a scan path such as a second scan path. The distance between the first scan path and the second scan path is bigger than the diameter of the charged electron beam. Referring to previous exemplary figures, SEM 10 directs a charged electron beam towards wafer 30 to interact with a section 45 of line 44 along scan path 60(2,1). The charged particle beam diameter is about 3 nanometers while the distance between scan path 60(1,1) and 60(2,1) is about 25 nanometers. It is noted that these values may be altered without exceeding the scope of the invention.

Step 128 is followed by step 130 of collecting electrons scattered as a result of the interaction between the charged particle beam and the resist and of processing the detected electrons to provide another width measurement.

It is noted that steps 124–130 may be repeated many times (even up to hundreds or thousands of time per scanning window) and their width measurements are processed (usually by applying statistical analysis) to provide at least one critical measurement result.

Method 140 shown in FIG. 8 resembles method 120 but the first and second scan paths are characterized by including multiple consecutive samples, and wherein the distance between the first scan path and the second scan path is bigger than a distance between adjacent samples (whereas according to method 120 the distance between the first and second scan paths is bigger than the diameter of the charged electron beam). It is noted that this difference is illustrated at steps 128 and 148 accordingly. It is noted that the distance between scan paths is about 25 nanometers while the distance between consecutive samples is about 1.5 nanometers. It is noted that these values may be altered without exceeding the scope of the invention.

Second Embodiment

A section of a pattern may be re-examined for various reasons, such as but not limited to, a failure of a previous measurement, increasing the measurement accuracy, performing a precision test and the like. Said repetition may enhance the shrinkage effect of said section.

According to an aspect of the invention the location of scan paths are changed between examination sessions. An examination session includes multiple examinations that are processed to provide a critical dimension indication. An exemplary examination session can include the measurements of a single scanning window. According to this second embodiment, the locations of scan paths differ from one scanning window to another, even if the scanning windows overlap.

The change of the location of scan paths or even a change in the location of a scanning window can be responsive to a predefined pattern but may also be random or semi-random. A predefined pattern may introduce a predefined vertical shift between scan paths, while a semi-random and/or random scheme may provide various shifts.

Figure 5:
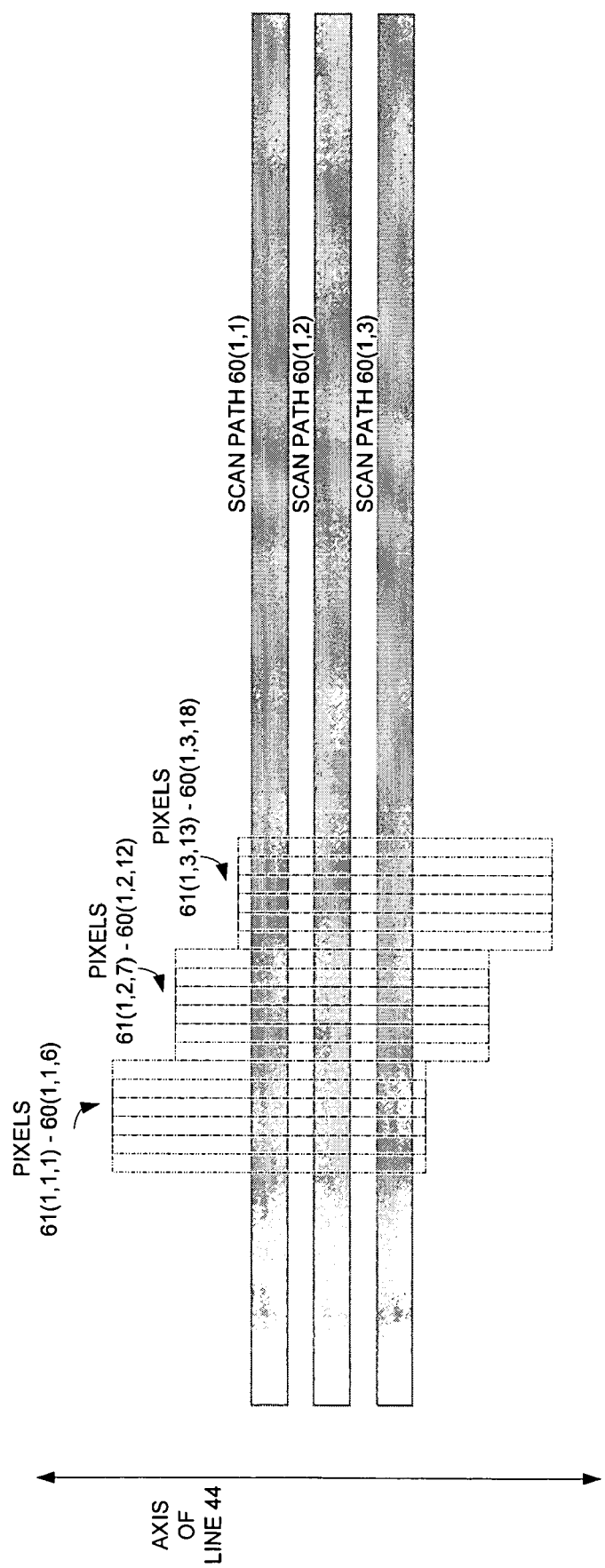

Referring to FIG. 5, three scan paths 60(1,1) and 60(1,2) and 60(1,3) that are scanned during three distinct measurement sessions and some corresponding pixels 61(1,1,1)–61(1,1,6), 61(1,2,7)–61(1,2,12) and 61(1,3,13)–61(1,3,18) are illustrated. Scan path 60(1,1) may be followed during a first measurement session, while scan path 60(1,2) is followed during a second measurement session, and scan path 60(1,3) is followed during a third measurement session. Scan paths 60(1,2) and 60(1,3) cause charged particles to interact with line 44 at distinct locations such that repetitive measurement sessions do not generate an additional shrink of the same inspected section.

Figure 9:
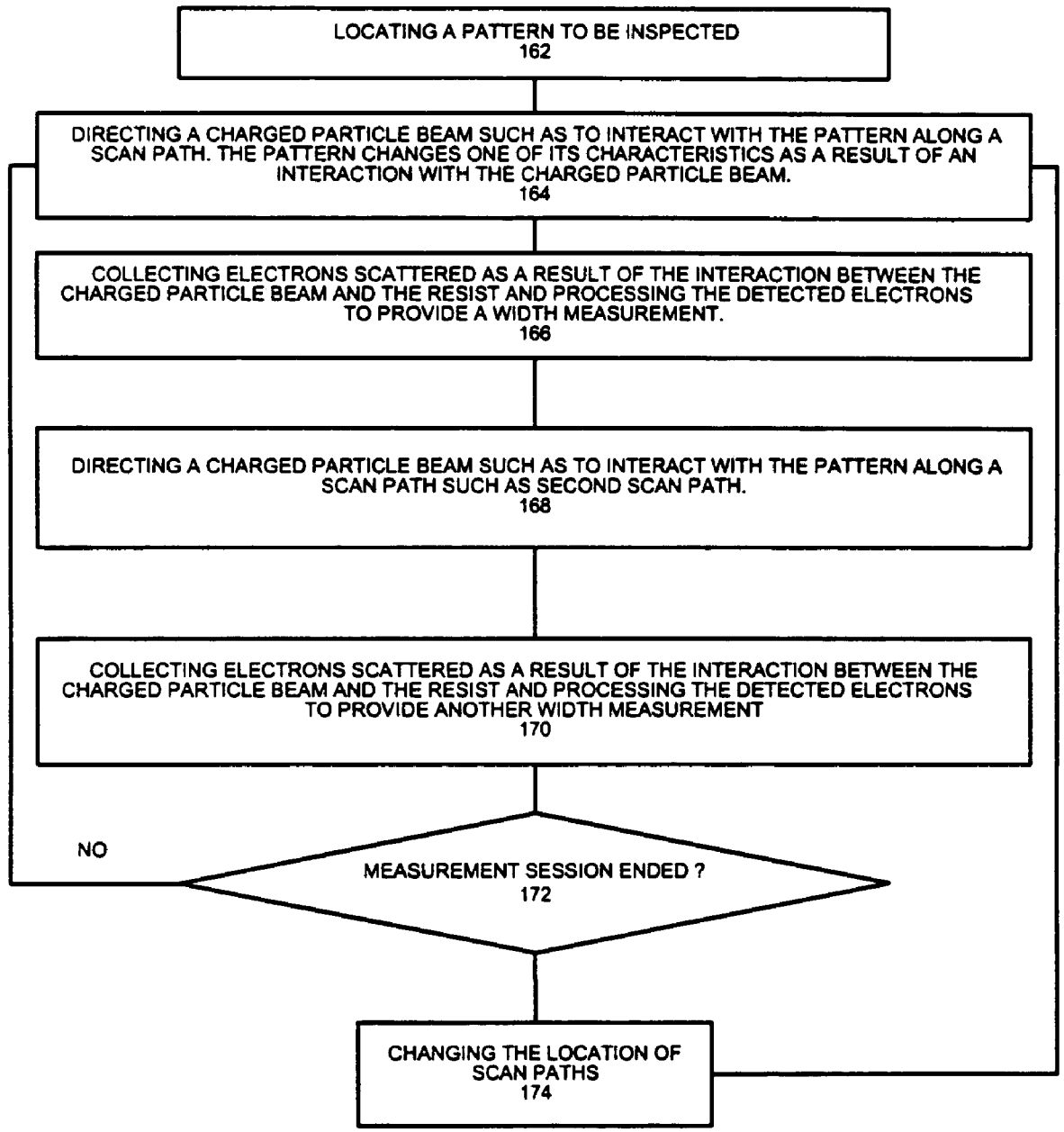

Referring to FIG. 9, method 160 in accordance with aspects of the invention is illustrated. During method 160 the locations of scan paths are altered between measurements and especially between measurement sessions.

Method 160 starts by step 162 of locating a pattern to be inspected, conveniently to have one of its dimensions measured. Referring to previous exemplary section 45 of line 44 is to be inspected in order to measure the width of line 44.

Step 162 is followed by step 164 of directing a charged particle beam such as to interact with the pattern along a scan path such as scan path 60(1,1). The pattern changes one of its characteristics as a result of an interaction with the charged particle beam. Referring to previous exemplary figures, SEM 10 directs a charged electron beam towards wafer 30 to interact with a section 45 of line 44 along scan path 60(1,1). It is noted that scan path 60(1,1) further interacts with other lines of portion 40. The change of characteristics is a shrinkage of the resist that forms line 44.

Step 164 is followed by step 166 of collecting electrons scattered as a result of the interaction between the charged particle beam and the resist and of processing the detected electrons to provide a width measurement.

Step 166 is followed by step 168 of directing a charged particle beam such as to interact with the pattern along a scan path such as second scan path 60(2,1). The distance between the first scan path and the second scan path is bigger than the diameter of the charged electron beam. Referring to previous exemplary figures, SEM 10 directs a charged electron beam towards wafer 30 to interact with a section 45 of line 44 along scan path 60(2,1). The charged particle beam diameter is about 3 nanometers while the distance between scan path 60(1,1) and 60(2,1) is about 25 nanometers. It is noted that these values may be altered without exceeding the scope of the invention.

Step 168 is followed by step 170 of collecting electrons scattered as a result of the interaction between the charged particle beam and the resist and of processing the detected electrons to provide another width measurement.

Step 170 is followed by step 172 of determining whether a measurement session has ended. If a measurement session did not end, step 172 is followed by step 164. It is noted that steps 164–170 may be repeated many times (even up to hundreds or thousands of time per scanning window) and their width measurements are processed (usually by applying statistical analysis) to provide at least one critical measurement result. If the measurement session ends and (not illustrated) there is a need to re-examine substantially the same section again, step 172 is followed by step 174 of changing the locations of the scan paths, and jumping to step 164. It is noted that the locations of the scan paths may be stored for future use, such as repeating a measurement. It is further noted that the locations of scan paths may be changed regardless of measurement sessions, and in such a case the method will have to determine when to change the location of the scan patterns and to repeat the scanning steps.

Third Embodiment

In many cases the system resolution is much smaller than the line width roughness bandwidth. By shaping the charged particle beam in response to said distinct requirements, a lower charged particle beam density may achieved without reducing the system performance.

Figure 6:
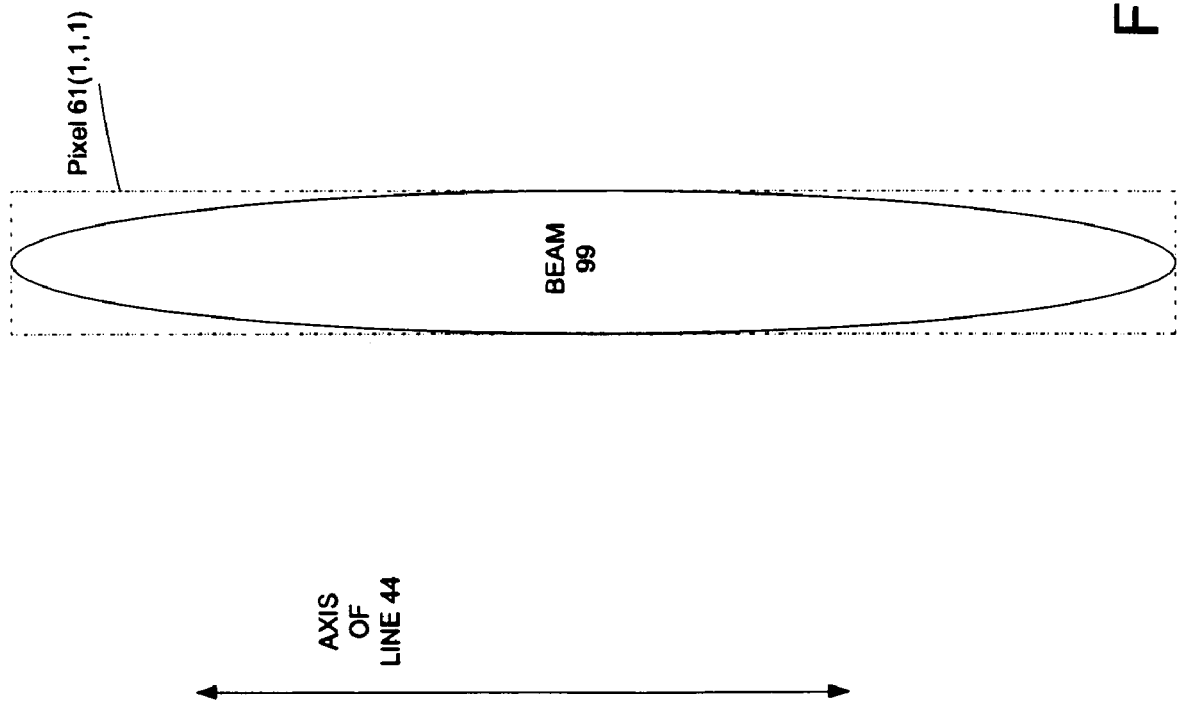

In other words, an ellipsoid beam instead of circular beam may be directed towards the wafer. For example, referring to FIG. 6, it is assumed that the width of pixel 61(1,1,1,) is about three nanometers and that the pixel length is about twenty five nanometers, then the beam 99 may be shaped as an ellipsoid having a major axis of about twenty five nanometers and a minor axis of about three nanometers.

The ellipse-shaped beam may be generated by introducing (or by not suppressing) axial and especially meridional astigmatism.

Referring to FIG. 10, method 180 in accordance with an aspect of the invention is illustrated. Method 180 starts by step 182 of locating a pattern to be inspected, conveniently to have one of its dimensions measured. Referring to previous examples section 45 of line 44 is to be inspected in order to measure the width of line 44.

Step 182 is followed by step 184 of directing a charged particle beam such as to interact with the pattern along a scan path such as first scan path 60(1,1). The beam is shaped in accordance with a rectangular pixel shape. Conveniently, the beam is shaped as an ellipsoid having a major axis substantially along an inspected pattern axis and a minor axis substantially perpendicular to the inspected pattern axis. The pattern changes one of its characteristics as a result of an interaction with the charged particle beam. Referring to previous exemplary figures, SEM 10 directs a charged electron beam towards wafer 30 to interact with a section 45 of line 44 along scan path 60(1,1). It is noted that scan path 60(1,1) further interacts with other lines of portion 40. The change of characteristics is a shrinkage of the resist that forms line 44. Line 44 is vertical and so is its pattern axis.

Step 184 is followed by step 186 of collecting electrons scattered as a result of the interaction between the charged particle beam and the resist and of processing the detected electrons to provide a width measurement.

Step 186 is followed by step 188 of directing a charged particle beam such as to interact with the pattern along a scan path such as second scan path.

Step 188 is followed by step 190 of collecting electrons scattered as a result of the interaction between the charged particle beam and the resist and of processing the detected electrons to provide another width measurement.

It is noted that steps 184–190 may be repeated many times (even up to hundreds or thousands of time per scanning window) and their width measurements are processed (usually by applying statistical analysis) to provide at least one critical measurement result.

We claim:

1. A method for scanning a pattern with a charged particle beam, the method comprising the steps of:
    directing the charged particle beam such as to interact with the pattern along a first scan path, wherein the pattern changes one of its characteristics as a result of an interaction with the charged particle beam; and
    directing the charged particle beam such as to interact with the pattern along a second scan path, wherein a separation distance between the first scan path and the second scan path is nowhere less than a diameter of the charged particle beam.

2. The method of claim 1 wherein the pattern is substantially made of a resist.

3. The method of claim 1 wherein the charged particle beam is an electron beam.

4. The method of claim 1 further comprising a step of collecting charged particles resulting from the interactions with the pattern.

5. The method of claim 4 further comprising a step of processing collected charged particles.

6. The method of claim 5 wherein the processing comprises providing an indication of a critical dimension of the pattern.

7. The method of claim 1 further comprising a preliminary step of locating the pattern.

8. A method for scanning a pattern with a charged particle beam, the method comprising the steps of:
    directing the charged particle beam such as to interact with the pattern along a first scan path, wherein the pattern changes one of its characteristics as a result of an interaction with the charged particle beam; and
    directing the charged particle beam such as to interact with the pattern along a second scan path,
    wherein each of the first and second scan paths comprise a plurality of consecutive samples, and a separation distance between the first scan path and the second scan path is nowhere less than a distance between adjacent samples.

9. The method of claim 8 wherein the pattern is substantially made of a resist.

10. The method of claim 8 wherein the charged particle beam is an electron beam.

11. The method of claim 8 further comprising a step of collecting charged particles resulting from the interactions with the pattern.

12. The method of claim 11 further comprising a step of processing collected charged particles.

13. The method of claim 12 wherein the processing comprises providing an indication of a critical dimension of the pattern.

14. The method of claim 8 further comprising a preliminary step of locating the pattern.

15. A method for scanning a pattern with a charged particle beam, the method comprising the steps of:
    within a first measurement session, directing the charged particle beam such as to interact with the pattern along a first scan path wherein the pattern changes one of its characteristics as a result of an interaction with the charged particle beam;
    directing the charged particle beam such as to interact with the pattern along a second scan path, wherein a separation distance between the first scan path and the second scan path is nowhere less than a diameter of the charged particle beam; and
    changing the location of the first scan path and the second scan path and repeating within a second measurement session the steps of directing the charged particle beam.

16. The method of claim 15 wherein the pattern is substantially made of a resist.

17. The method of claim 15 wherein the charged particle beam is an electron beam.

18. The method of claim 15 further comprising a step of collecting charged particles resulting from the interactions with the pattern.

19. The method of claim 18 further comprising a step of processing collected charged particles.

20. The method of claim 19 wherein the processing comprises providing an indication of a critical dimension of the pattern.

21. The method of claim 15 further comprising a preliminary step of locating the pattern.

22. An apparatus for scanning a pattern with a charged particle beam, the apparatus comprising:
    means for generating the charged particle beam; and
    means for directing the charged particle beam such as to interact with the pattern along a first scan path, wherein the pattern changes one of its characteristics as a result of an interaction with the charged particle beam, the means for directing are further operable to direct the charged particle beam such as to interact with the pattern along a second scan path, and a separation distance between the first scan path and the second scan path is nowhere less than a diameter of the charged particle beam.

23. An apparatus for scanning a pattern with a charged particle beam, the apparatus comprising:
    means for generating the charged particle beam; and
    means for directing the charged particle beam such as to interact with the pattern along a first and second scan paths, each of the first and second scan paths comprising a plurality of consecutive samples, wherein the pattern changes one of its characteristics as a result of an interaction with the charged particle beam, and a separation distance between the first scan path and the second scan path is nowhere less than a distance between adjacent samples.

24. An apparatus for scanning a pattern with a charged particle beam, the apparatus comprising:
   means for generating the charged particle beam; and
   means for directing the charged particle beam within a first measurement session such as to interact with the pattern along a first scan path and a second scan path, wherein a separation distance between the first scan path and the second scan path is nowhere less than a diameter of the charged particle beam and the pattern changes one of its characteristics as a result of an interaction with the charged particle beam, and
   the means for directing are further operable to change the location of the first scan path and the second scan path when repeating the directing of the charged particle beam within a second measurement session.

* * * * *